United States Patent [19]
Muhler et al.

[11] 4,108,981
[45] Aug. 22, 1978

[54] ALKALINE ORAL COMPOSITIONS COMPRISING ALUMINUM AND A CARBOXYLIC ACID

[75] Inventors: Joseph C. Muhler, Howe; Mark S. Putt; Carl J. Kleber, both of Fort Wayne, all of Ind.

[73] Assignee: Indiana University Foundation, Bloomington, Ind.

[21] Appl. No.: 710,439

[22] Filed: Aug. 2, 1976

[51] Int. Cl.$^2$ .............................................. A61K 7/24
[52] U.S. Cl. ...................................... 424/55; 424/49; 424/52
[58] Field of Search ................... 424/48–58; 51/307–309

[56] References Cited

U.S. PATENT DOCUMENTS

| | | | |
|---|---|---|---|
| 1,275,275 | 8/1918 | Levinson | 424/49 |
| 1,467,024 | 9/1923 | Bergve | 424/49 |
| 1,528,422 | 3/1925 | Helsloy | 424/55 |
| 1,619,076 | 3/1927 | Kuever | 424/55 |
| 3,034,967 | 5/1962 | Apperson et al. | 424/52 |
| 3,095,356 | 6/1963 | Moss | 424/52 |
| 3,105,013 | 9/1963 | Saul et al. | 424/52 |
| 3,124,506 | 3/1964 | Holman | 424/55 |
| 3,151,028 | 9/1964 | Hay et al. | 424/55 |
| 3,282,792 | 11/1966 | Fiscella | 424/52 |
| 3,577,521 | 5/1971 | Scholler et al. | 424/55 |

FOREIGN PATENT DOCUMENTS

| | | |
|---|---|---|
| 829,272 | 12/1969 | Canada. |
| 3610M | 11/1965 | France. |
| 176,091 | 4/1948 | Japan. |
| 74/24,224 | 6/1974 | Japan. |
| 1,287,758 | 9/1972 | United Kingdom. |

OTHER PUBLICATIONS

Gerhardt et al., J. Dent. Res. 51(3), 870, May–Jun., 1972, Fluoride Uptake in Natural Tooth Surfaces Pretreated with Aluminum Nitrate.

Ericsson Chem. Abstr. 59, No. 7315c (1963) of Acta. Odontol. Scan. 20: 441–451 (1962) Aluminum Compounds in Fluorinated Toothpastes and Dental Prophylaxis Pastes.

*Primary Examiner*—Shep K. Rose
*Attorney, Agent, or Firm*—Kirkland & Ellis

[57] ABSTRACT

Improved anticariogenic oral compositions comprise a non-toxic and anticariogenically effective amount of one or more water-soluble alumium salts, a non-toxic stable complexing carboxylic acid or water-soluble salt thereof, and a carrier suitable for use in the oral cavity at a pH of about 7.0–9.0.

10 Claims, No Drawings

ALKALINE ORAL COMPOSITIONS COMPRISING ALUMINUM AND A CARBOXYLIC ACID

BACKGROUND OF THE INVENTION

1. Field of the Invention

The invention relates to therapeutic oral products such as dentifrices, mouthwashes, prophylaxis pastes, topical solutions and the like and more particularly to oral compositions providing aluminum ions in therapeutically effective biologically available form.

2. Description of the Prior Art

It is commonly recognized that the presence of small amounts of fluoride in occurring naturally drinking water (e.g., 1.0 microgram fluoride per milliliter) has a pronounced effect in reducing the incidence of dental caries in permanent teeth of children consuming such water from birth through eight years of age. Fluoride salts have been introduced into public water supplies in many communities with similar results. This method of dental caries prophylaxis is not available, however, to large numbers of people whose drinking water is obtained from small, private, fluoride-deficient sources such as individual wells and the like. Further, the addition of fluoride to common public water sources is not always accepted or permitted.

Topical application of aqueous fluoride solutions by dentists or dental hygienists likewise provide an excellent measure of protection against dental caries. Various fluoride compounds have been employed in this manner, including, stannous fluoride and sodium fluoride. Another method of employing the anticariogenic properties of fluoride salts comprises incorporating such materials with a compatible abrasive to form a prophylactic paste composition for use by dentists or dental hygienists on a professional basis.

Limitations on the availability of fluoride therapy by way of water supply or professional treatment had led to extensive efforts to incorporate fluoride salts in oral compositions for use in the home in the form of fluoride-containing dentifrices. Although effective dental caries protection has been obtained through the use of the aforementioned fluoride-containing compounds, occasional side effects have been experienced with certain of the known fluoride-containing anticariogenic agents, particularly certain tin-containing salts. For example, a brownish pigmentation of carious or precarious lesions has been experienced after anticariogenic agents containing the stannous ion have been applied to the teeth when the teeth are not properly cleaned with a toothbrush. Although the stain is not necessarily undesirable from a physiological standpoint, nevertheless, for esthetic reasons it would be desirable to provide an effective anticariogenic agent that does not pigment carious enamel.

The utility of certain of the prior art anticariogenic fluoride materials has also been limited by the extent of their solubility in aqueous media. For example, sodium fluoride is only soluble to the extent of about 4% in water.

Furthermore, because of the concern from a toxicity standpoint, current regulations imposed by the U.S. Food and Drug Administration limit the amount of fluoride that can be provided in products sold for over-the-counter use.

Finally, certain of the known prior art anticariogenic agents have been relatively unstable in aqueous solution. For example, stannous fluoride is subject to both oxidation and hydrolysis and for that reason must be used in freshly prepared form and must be used in conjunction with complexing anions in order to obtain its optimal anticariogenic effect.

For the foregoing and other reasons, dental researchers have continued their efforts to develop new anticariogenic agents which not only demonstrate a high level of anticariogenic effectiveness in comparison with fluorides but which are non-toxic, stable, and widely available. It has been suggested that aluminum salts may have a beneficial effect in reducing dental caries or in facilitating the uptake of fluoride by the dental enamel. See, e.g., Manly et al., "Substances Capable of Decreasing the Acid Solubility of Tooth Enamel", J. Dent. Res. 28: 160 (1948); Regolati, et al., "Effects of Aluminum and Fluoride on Caries, Fluorine Content and Dissolution of Rat Molars", Hel. Odon. Acta. 13: 59 (1969; and Kelada, "Electro-chemical Characteristics of Free and Complexed Fluorides in Drinking Water and The Effects of Aluminum and Iron on Fluoride Incorporation Into Tooth Enamel," Univ. Michigan Thesis (1972).

In vitro studies have shown that pretreatment of enamel with aluminum solutions resulted in increased fluoride uptake when followed by treatment with a fluoride solution; however, treatment with combinations of aluminum and fluoride did not afford any added benefit over that of fluoride alone. McCann, "The Effect of Fluoride Complex Formation on Fluoride Uptake and Retention in Human Enamel", Archs. Oral Biol. 14:521 (1969); and Gerhardt, et al., "Fluoride Uptake in Natural Tooth Surfaces Pretreated with Aluminum Nitrate", J. Dent. Res. 51:870 (1972). Moreover, the foregoing techniques have dealt primarily with the use of aluminum in combination with fluorides in acidic media and have not focussed on the effect of aluminum in the absence of fluoride and in alkaline media.

Thus, while some elements are known to inhibit dental caries (e.g., F, Mo, Sr, and V) and while others are known to promote caries (e.g., Se, Mg, and Cd), the preponderance of data on aluminum indicate that it is dental caries inert as classified by Navia, "Effect of Minerals on Dental Caries", in *Dietary Chemicals vs. Dental Caries*, A.C.S., Washington, D. C. (1970).

Nor has the use of aluminum salts in dentifrices demonstrated the desired result, primarily because it has not been recognized that conventional dentifrice constituents such as abrasives are incompatible with sources of biologically available aluminum. Thus, while French Pat. No. 3610M describes a specific combination of aluminum lactate, aluminum fluoride and calcium pyrophosphate, the abrasive interferes with the aluminum by reacting therewith to form insoluble aluminum phosphate. Similarly, U.S. Pat. No. 3,095,356 uses aluminum salts such as aluminum fluoride to coact with insoluble sodium metaphosphate abrasives to reduce the solubility of such abrasives and to increase fluoride uptake, but without independent therapeutic advantage being taken of the aluminum.

U.S. Pat. No. 3,282,792 describes low pH stannous fluoride dentifrices stabilized against precipitation and oxidation of stannous tin ions through the use of hydroxyl substituted di- and tri-carboxylic acids. However, nothing is said in the patent regarding the use of aluminum with respect to anticariogenic systems that do not contain fluoride. Similarly, while U.S. Pat. 3,937,806 teaches oral compositions comprising indium and fluoride to which malic acid is added to stabilize the indium, the patent does not recognize that beneficial results may be achieved with aluminum and carboxylic acids without incorporating fluoride.

Canadian Pat. No. 829,272 describes acidic dentrifices comprising a combination of surface active substances and albumen coagulating substances such as certain carboxylic acid salts of aluminum and other metals. However, this patent likewise fails to teach that the satisfactory use of aluminum ions in dentifrices is dependent upon the use of aluminum-compatible constituents or that significant dental health benefits can be achieved with alkaline aluminum systems.

Thus, the prior art has not heretofore suggested a therapeutically effective system which provides biologically available aluminum in an anticariogenic oral composition, especially one operative at high pH and in the absence of fluoride.

Accordingly, a primary object of the present invention is to provide oral compositions incorporating water-soluble salts in stable biologically available and therapeutically effective form.

A further object is to provide anticariogenic oral compositions comprising water-soluble aluminum salts and complexing carboxylic acids.

Another object is to provide new oral compositions for dental caries prophylaxis.

SUMMARY OF THE INVENTION

The foregoing and other objects, advantages, and features of the subject invention may be obtained with anticariogenic oral compositions comprising a nontoxic and anticariogenically effective amount of at least one water-soluble aluminum salt, a non-toxic amount of a stable, complexing carboxylic acid or water-soluble salt thereof, and a carrier suitable for use in the oral cavity at a pH lying in the range of about 7.0–9.0.

The aqueous aluminum-carboxylic acid complexes formed in accordance with invention serve to maintain aluminum ions in available form (i.e., such that they are not removed by formation of insoluble precipitates) and yet the aluminum is not bound so tightly that it is not free to act on dental enamel and prevent or arrest dental caries.

DETAILED DESCRIPTION OF THE PREFERRED EMBODIMENTS

In general, the present invention comprises oral compositions containing an anticariogenically effective and non-toxic amount of one or more water-soluble aluminum salts, a non-toxic amount of a stable complexing carboxylic acid or water-soluble salt thereof, and a carrier suitable for use in the oral cavity at a pH of 7.0–9.0.

The term "oral composition" as used in this application refers to a product which in the ordinary course of usage is not intentionally ingested but which is retained in the oral cavity for a sufficient time to contact the teeth. Such products include, by way of example, dentifrices, mouthwashes, dental prophylaxis pastes, topical solutions, chewing gums, and the like. Suitable carriers in accordance with this invention including the cleaning and polishing abrasives and other constituents of dentifrices and dental prophylaxis pastes and water in the case of mouthwashes and topical solutions.

The particular water-soluble aluminum salt employed is not critical, and substantially any nontoxic water-soluble aluminum ion containing salt may be used. Suitable aluminum salts include aluminum potassium sulfate, $AlK(SO_4)_2 \cdot 12H_2O$; aluminum chloride, $AlCl_3 \cdot 6H_2O$; aluminum sodium sulfate, $AlNa(SO_4)_2 \cdot 12H_2O$; aluminum ammonium sulfate, $AlNH_4(SO_4)_2 \cdot 12H_2O$; aluminum sodium phosphate, $NaAl_3H14(PO_4)_8 \cdot 4H_2O$; aluminum sulfate, $Al_2(SO_4)_3 \cdot 18H_2O$; aluminum nitrate, $Al(NO_3)_3 \cdot 9H_2O$; and sodium aluminate, $NaAl(OH)_4$. Aluminum potassium sulfate and aluminum chloride are preferred by reason of their wide availability and well established safety.

The anticariogenically effective and nontoxic amount of the soluble aluminum salt should lie in the range capable of supplying about 10 ppm up to about 50,000 ppm aluminum ions, 0.001–5.0 weight percent (calculated as aluminum ion). Thus, where aluminum potassium sulfate dodecahydrate and aluminum chloride hexahydrate are employed, the respective salts are present in the range of about 0.02 up to about 75% and about 0.01 up to about 45% by weight.

The stable complexing carboxylic acids that are employed in accordance with this invention include acetic and citric acid acid and such dicarboxylic and hydroxdicarboxylic acids as malic acid, tartaric acid, fumaric acid, adipic acid, succinic acid, and the like. Mixtures of such acids may be employed as well, as may the sodium, potassium, ammonium, and other water-soluble salts thereof. Toxic carboxylic acids are beyond the scope of this invention as are those carboxylic acids, such as lactic acid, which would be unstable under the conditions of use.

While benefits may be achieved with the presence of any appreciable amounts of the complexing carboxylic acids of this invention, optimal results appear to be achieved where the carboxylic acid is present in a molar ratio of approximately 1:1 based on the aluminum ions. Anticariogenic effectiveness does not appear to be enhanced with molar ratios of acid to aluminum ion that exceed 1:1 although the biological availability of the aluminum ion does not appear to be adversely affected thereby.

Preferably, the carboxylic acid is present at a level of about 0.05–2.5%, by weight. Preferred carboxylic acids in accordance with this invention are malic acid and tartaric acid by reason of their ready availability, lack of toxicity, and the fact that the complexes they form with aluminum appear to be sufficiently strong to prevent the aluminum from being deactivated by other constituents yet they bind the aluminum sufficiently loosely to permit it readily to coact with the dental enamel.

If desired, one or more fluoride-containing anticariogenic adjuvants may also be incorporated in the oral preparations in accordance with this invention. Preferably, the adjuvant is present in the form of water-soluble fluoride-containing compounds capable of supplying fluoride. The preferred adjuvant is sodium fluoride, NaF, although other materials such as stannous fluorozirconate ($SnZrF_6$), indium fluorozirconate ($InZrF_7$), stannous fluoride ($SnF_2$), and complex zirconium-germanium fluorides [e.g., $Zr(GeF_6)_2$, $ZrGeF_8$, $Ge(ZrF_6)_2$, and $ZrOGeF_6$] may be employed. Sodium fluoride is preferred by virtue of the absence of objectionable taste, lack of enamel pigmentation, and the freedom from damage to gingival tissue, and by reason of anticariogenic effectiveness obtainable therewith.

Other suitable adjuvants include water-soluble fluoride salts such as $NH_4F$, $SnF_4$, KF, $InF_3$, $PbF_2$, and LiF, as well as more complex water-soluble fluoride-containing adjuvants such as fluorosilicates, e.g., $Na_2SiF_6$, other fluorozirconates, e.g., $CaZrF_6$, $Na_2ZrF_6$, $K_2ZrF_6$, fluorostannites, e.g., $NaSnF_3$, fluoroborates, e.g., NaBF$_4$, fluorotitanates, e.g., NaTiF$_5$, other fluorogermantes, e.g., K$_2$GeF$_6$, and mixed halides, e.g., SnClF and Sn$_2$ClF$_3$. Mixtures of suitable adjuvants may also be utilized.

In general, fluoride-containing oral compositions produced in accordance with the subject invention will contain from about 0.05 up to 1.0%, by weight, of the fluoride-containing anticariogenic adjuvant so as to desirably provide about 1000 ppm fluoride ion. Sodium fluoride is preferably provided at a level of 0.22%, by weight, and when SnF$_2$ is utilized, the desired amount is preferably about 0.4%.

The natural pH values of the oral compositions of this invention lie in the range of about 1.0 to 4.0, and in accordance with this invention the pH should be adjusted in the range of about 7.0-9.0 with sodium hydroxide or other buffering agents. An especial advantage of the compositions of this invention is that they may be employed at neutral or in weakly alkaline pH, conditions under which aluminum could not ordinarily be present due to the formation of insoluble aluminum compounds.

DENTIFRICE PREPARATIONS

Oral compositions adapted for regular home use such as dentifrice preparations and the like typically comprise about 10-95%, by weight, of a compatible cleaning and polishing agents as a carrier suitable for use in the oral cavity.

Various compatible cleaning and polishing agents, suitable for use in dentifrice preparations include purified, calcined kaolin abrasives disclosed in applicant's co-pending application entitled "DENTIFRICE PREPARATIONS COMPRISING PURIFIED, CALCINED KAOLIN ABRASIVES", Ser. No. 710,444, field herewith; calcined aluminum silicate abrasives of the type described in U.S. Pat. No. 3,105,013, commercially available under the trademark "Kaopolite SF"; zirconium silicate as described and claimed in U.S. Pat. No. 3,450,813; calcined and uncalcined talcs, Mg$_3$Si$_4$O$_{10}$(OH)$_2$; resin abrasives as described in U.S. Pat. No. 3,070,510; barium sulfate; silica; alumina; and mixtures thereof. Mixtures of such abrasives may also be employed. Preferably, purified, calcined kaolin abrasives are employed in such dentifrice preparations.

Dentifrice preparations in accordance with the subject invention are prepared in a conventional manner and usually include additional ingredients which render the over-all composition commercially acceptable to consumers.

Thus, toothpastes require a binder substance to impart desired textural properties. Alkoxylated cellulose derivatives, nonionic agents resulting from the addition of ethylene oxide to a condensation product of propylene oxide and propylene glycol, natural gum binders such as gum tragancanth, gum karaya, gum arabic, etc., and seaweed derivatives such as Irish moss and alginates, and water-soluble cellulose derivatives, such as sodium carboxymethyl cellulose can be used for this purpose. Synthetic colloidal magnesium silicate, such as "Laponite", also may be used and is preferred in gel-type formulations. Desirably, those materials are employed which are most compatible with aluminum ions. Improvements in texture can also be attained by including an additional material such as colloidal magnesium aluminum silicate or colloidal silica. Binders in an amount of from 0.5% to 5.0%, by weight, can be used to form a satisfactory toothpaste.

Toothpastes conventionally contain sudsing agents. Suitable sudsing agents include, but are not limited to, water soluble alkyl sulfates having from 8 to 18 carbon atoms in the alkyl radical, such as sodium lauryl sulfate, ethoxylated fatty ethers or ethoxylated fatty alcohol esters, water-soluble salts of sulfonated monoglycerides of fatty acids having from 10 to 18 carbon atoms in the alkyl radical such as sodium coconut monoglyceride sulfonate, salts of fatty acid amides of taurines such as sodium-N-methyl palmitoyl taurine, nonionic surfactants, and salts of fatty acid esters of isethionic acid. Sudsing agents can be used in the compositions of this invention in an amount of from about 0.5% to about 5.0%, by weight, of the total composition.

It is also desirable to include an humectant material in a toothpaste to prevent hardening. Materials commonly used for this purpose include glycerine, sorbitol, and other polyhydric alcohols. The humectants can comprise up to 35% of conventional toothpaste compositions. In the case of gel-type formulations, humectants may be used at levels as high as 80%, by weight.

Finally, flavoring materials may be included in a toothpaste formulation including small amounts of oils of wintergreen and peppermint and sweetening agents such as saccharin, dextrose, and levulose.

Compositions of exemplary dentifrice preparations employing the oral compositions of the present invention are given in the following Examples.

EXAMPLE I

| Constituent | Parts by Weight |
| --- | --- |
| Purified, calcined kaolin | 37.00 |
| Aluminum chloride | 0.89 |
| Malic Acid | 0.50 |
| Water | 21.51 |
| Glycerine | 14.00 |
| Sorbitol | 17.50 |
| Fumed silica | 2.00 |
| Xanthan gum | 1.50 |
| Sodium lauryl sulfate | 1.50 |
| Sodium hydroxide (50%) | 1.60 |
| Flavorings, coloring, etc. | 2.00 |
| | 100.00 |

EXAMPLE II

| Constituent | Parts by Weight |
| --- | --- |
| Calcined aluminum silicate | 37.00 |
| Aluminum potassium sulfate | 1.76 |
| Tartaric Acid | 0.56 |
| Water | 19.08 |
| Glycerine | 14.00 |
| Sorbitol | 17.50 |
| Fumed silica | 4.50 |
| Xanthan gum | 0.50 |
| Sodium lauryl sulfate | 1.50 |
| Sodium hydroxide (50%) | 1.6 |
| Flavorings, colorings, etc. | 2.00 |

The foregoing Examples may be altered by using other carboxylic acids, abrasives, and aluminum salts. An exemplary fluoride containing dentrifice in accordance with this invention is given below.

EXAMPLE III

| Constituent | Parts by Weight |
| --- | --- |
| Purified, calcined kaolin | 37.00 |
| Aluminum chloride | 0.52 |
| Sodium citrate (hydrous) | 0.10 |
| Sodium fluoride | 0.22 |
| Water | 25.66 |
| Glycerine | 14.00 |
| Sorbitol | 17.50 |
| Xanthan gum | 1.50 |
| Sodium lauryl sulfate | 1.50 |
| Flavorings, colorings | 2.00 |

EXAMPLE III-continued

| Constituent | Parts by Weight |
| --- | --- |
| | 100.00 |

Suitable gel-type dentrifices and toothpowders are given in the following Examples.

EXAMPLE IV

| Gel-Type | |
| --- | --- |
| Constituent | Parts by Weight |
| Precipitated silica | 22.00 |
| Aluminum potassium sulfate | 1.02 |
| Malic Acid | 0.50 |
| Water | 3.07 |
| Glycerine | 4.05 |
| Sorbitol | 64.16 |
| Carboxymethyl cellulose | 0.20 |
| Laponite 2101 | 1.05 |
| Sodium lauryl sulfate | 1.50 |
| Flavorings, colorings, etc. | 2.00 |
| | 100.00 |

EXAMPLE V

| Toothpowder | |
| --- | --- |
| Constituents | Parts by Weight |
| Purified, calcined kaolin | 70.00 |
| Aluminum nitrate | 1.4 |
| Malic acid | 0.5 |
| Fillers | 26.8 |
| Flavorings, etc. | 2.3 |
| | 100.0 |

PROPHYLACTIC PASTE COMPOSITIONS

Oral compositions of the present invention include, in addition to the described dentifrice preparations, prophylactic paste compositions adapted for relatively infrequent application (e.g., once or twice a year), either professionally (i.e., by a dentist or dental hygienist) or by self-application under professional supervision. A prophylactic paste composition generally differs from a dentifrice composition in that the cleaning and polishing component thereof is more abrasive (and as a result, is a better tooth cleaner). Since a prophylactic paste composition is applied only once or twice per year, a more abrasive cleaning and polishing agent may safely be employed therein than in a dentifrice preparation (i.e., if the more abrasive cleaning and polishing agent were used in a dentifrice preparation adapted for frequent application, the agent might permanently damage the oral hard tissues).

The compatible substances previously described as suitable cleaning and polishing agents for incorporation in dentifrice preparations may also be employed as the cleaning and polishing component of prophylactic paste compositions. However, in order that the desired optimal level of cleaning and polishing effectiveness be obtained, a different particle size and surface configuration for the substance is needed. For example, a suitable zirconium silicate preparation for use in a dentifrice preparation is disclosed and claimed in U.S. Pat. No. 3,450,813, and suitable zirconium silicate cleaning and polishing agents for use in a prophylactic paste composition is described and claimed in U.S. Pat. Nos. 3,257,282, and 3,330,732.

Prophylactic paste compositions in accordance with the present invention are formulated from about 0.01 to about 50.0% and preferably about 1-15% of a soluble aluminum salt and about 0.05 to about 25% and preferably about 0.5-7.5% of a complexing carboxylic acid. The cleaning and polishing agent serves as a carrier and is employed with a range of about 20 to 80% by weight depending on the particular formulations as is well known to one skilled in the art.

The prophylactic paste compositions are prepared in a conventional manner and usually include additional ingredients that render the overall composition commercially acceptable. For example, prophylactic paste compositions typically embody conventional components such as bleaching agents, binders, humectants, flavoring agents and the like. A preferred prophylactic paste composition produced in accordance with the present invention is given hereinafter as Example VI.

EXAMPLE VI

| Constituent | Parts by Weight |
| --- | --- |
| Zirconium silicate | 50.0 |
| Aluminum nitrate | 10.0 |
| Tartaric acid | 2.5 |
| Sodium lauryl sulfate | 0.5 |
| Binders | 2.0 |
| Humectants | 20.0 |
| Water | 14.0 |
| Flavorings, colorings, etc. | 1.0 |
| | 100.0 |

OTHER ORAL COMPOSITIONS

In addition to dentifrices and prophylactic pastes, the present invention may be used in conjunction with other compositions (e.g., topical solutions and mouthwashes) comprising aluminum salts in the range of about 0.1–50% and complexing carboxylic acids in the range of about 0.05–25% as shown in the follow Examples.

EXAMPLE VII

| Topical Solution | |
| --- | --- |
| Constituent | % by Weight |
| Aluminum chloride | 10 |
| Citric acid | 1 |
| Water | 89 |
| | 100 |

The pH is adjusted with $N_2OH$ to about 8.0.

EXAMPLE VIII

| Mouthwash Preparation | |
| --- | --- |
| Constituent | % by Weight |
| Sodium aluminate (9.073% aluminum solution) | 1.10 |
| Malic acid | .50 |
| Water | 71.59 |
| Sorbitol | 8.00 |
| Glycerin | 5.00 |
| Ethanol (95%) | 12.00 |
| Flavor, coloring, etc. | 1.81 |
| | 100.00 |

EXPERIMENTAL EVALUATIONS

The significant anticariogenic benefits of the aluminum-carboxylic acid oral compositions of this invention have been demonstrated in dental caries studies performed with rats, standard experimental animals for dental purposes. A total of 156 weanling (28 day old) Wistar strain rats were randomly divided into 8 equal groups according to sex, body weight, and litter mates. The parents of the weanlings were placed on a low fluoride corn diet and fluoride-free redistilled drinking water one week prior to mating. The mother rats were maintained on this same regimen during their 21 day gestation period and the subsequent 28 day weaning period following the birth of the pups. This procedure eliminates exposure of the pups to any exogenous sources of fluoride during their development.

After weaning, the 28-day old rats were placed on a low fluoride stock corn caries inducing diet and fluoride-free redistilled water ad libitum. Once daily 5 days per week the right and left mandibular molars were each swabbed for one minute with the respective topical treatment solution. A cotton swab was used to apply the solution to the molars by freshly dipping into the solution every 15 seconds during the 1 minute treatment. The topical solutions used for treatment were as follows:

| | | pH |
|---|---|---|
| Group 1 | 200 ppm $Al^{+3}$ (as $AlCl_3 \cdot 6H_2O$) + 0.1% acetic acid | Adjusted to $4.1 \pm 0.1$ |
| Group 2 | 200 ppm $Al^{+3}$ (as $AlCl_3 \cdot 6H_2O$) + 0.38% lactic acid | Adjusted to $7.9 \pm 0.1$ |
| Group 3 | 200 ppm $Al^{+3}$ (as $AlCl_3 \cdot 6H_2O$) + 250 ppm $F-$ (as NaF) + 0.1% malic acid | Adjusted to $4.1 \pm 0.1$ |
| Group 4 | 200 ppm $Al^{+3}$ (as $AlCl_3 \cdot 6H_2O$) + 250 ppm $F-$ (as NaF) + 0.1% malic acid | Adjusted to $7.9 \pm 0.1$ |
| Group 5 | 250 ppm $F-$ (as $SnF_2$) | Adjusted to $4.1 \pm 0.1$ |
| Group 6 | Fluoride-free redistilled water (control) | Natural |
| Group 7 | Fluoride-free redistilled water (control) | Natural |
| Group 8 | 200 ppm $Al^{+3}$ (as $AlCl_3 \cdot 6H_2O$) + 0.1% malic acid | Adjusted to $7.9 \pm 0.1$ |

The pH of the 200 ppm $Al^{+3}$ solution was adjusted by adding glacial acetic acid to a final concentration of 0.1% followed by addition of NaOH until pH 4.1 was reached. The pH of all other solutions was adjusted using NaOH. All solutions were prepared 3 days prior to initiation of the study except the $SnF_2$ treatment solution which must be prepared fresh daily. These original stock solutions were used throughout the entire study, except for the 200 ppm $Al^{+3}$ + 0.38% lactic acid solution which was prepared fresh once a week due to instability.

The rats were housed in an air-conditioned room in cages with raised screen floors, and the usual sanitary measures in the care of laboratory animals were strictly followed. The lights were time regulated to insure 12 hours of light and 12 hours of darkness.

The weight of the rats was determined initially, and then at one-month periods until the conclusion of the study. The control animals in Group 7 were periodically sacrificed during the study to determine when the carious process had reached the proper stage for analysis. For this animal study it was necessary to continue the study for 11 weeks in order for an adequate degree of dental caries to have developed. After the 11-week period the animals were sacrificed by chloroform inhalation. The mandibles were removed and placed in 10% formalin for two days, then stored in 70% ethanol until the time of examination. All animals were coded in order to prevent identification of the treatment groups by the examiners. The teeth were dried with air and the incidence and severity of the caries determined using a binocular dissecting microscope at 20X magnification. Dental caries were determined with the aid of a sharp dental explorer and tabulated accurately on an examination form according to location and size of the lesion. Briefly, the method of scoring for dental caries was as follows: each fissure cavity was counted as one lesion according to its location (incidence) — the first, second, and third molars have, respectively, three, two and one fissures (use of the stock corn diet induces only fissure caries). The size (severity) of the lesions was determined by arbitrarily classifying them as 1, 2, or 3, where 1 is the smallest that can be detected; 2 shows deep penetration into the dentin; and 3 is a destruction of the fissure or cusp with complete cavitation in the pulp chamber.

All the teeth were independently examined and classified blindly by two different examiners.

Dental caries data are given in the Table. In order to verify the results obtained in the foregoing study, the entire study was repeated, and the data from the replicate are also reported in the Table. The data from the two studies are also presented in combined form in the Table.

Numerically, all experimental groups demonstrated a reduction in dental caries. However, the results from both studies for aluminum plus acetic acid (Group 1) and the unstable aluminum plus lactic acid system (Group 2) were not statistically significant, but the results were significant for Groups 3, 4, and 8 (aluminum and malic acid with and without fluoride and at different pH) and for Group 5 (stannous fluoride). While the results achieved with the compositions of this invention were not significantly different from the reductions obtained with stannous fluoride, they nonetheless demonstrate that the objective of safely and effectively reducing dental caries has been achieved.

TABLE

| Group No. | Treatment Solution | Adjusted pH | STUDY #1 No. of Rats | STUDY #1 Caries Incidence | STUDY #1 % Reduction | STUDY #2 No. of Rats | STUDY #2 Caries Incidence | STUDY #2 % Reduction | Combined Data No. of Rats | Combined Data Caries Incidence | Combined Data % Reduction |
|---|---|---|---|---|---|---|---|---|---|---|---|
| 1 | 200 ppm $Al^{+3}$ + 0.1% acetic acid | 4.1 | 20 | $4.85 \pm 1.92$ | 18.5% | 19 | $3.95 \pm 2.32$ | 30.1% | 39 | $4.41 \pm 2.14$ | 24.0% |
| 2 | 200 ppm $Al^{3O}3$ + 0.38% lactic acid | 7.9 | 19 | $5.26 \pm 1.69$ | 11.7 | 19 | $4.37 \pm 1.46$ | 22.7 | 38 | $4.82 \pm 1.62$ | 16.9 |
| 3 | 200 ppm $Al^{3O}3$ + 250 ppm $F^-$(NaF) + 0.1% ppm malic acid | 4.1 | 18 | $4.00 \pm 1.49$ | 32.9 | 20 | $3.20 \pm 2.58$ | 43.4 | 38 | $3.58 \pm 2.15$ | 38.3 |
| 4 | 200 ppm $Al^{+3}$ + 250 ppm $F^-$(NaF) + 0.1% malic acid | 7.9 | 19 | $4.32 \pm 1.52$ | 27.5 | 20 | $4.05 \pm 2.16$ | 28.3 | 39 | $4.18 \pm 1.86$ | 27.9 |
| 5 | 250 ppm $F^-$($SnF_2$) | 4.1 | 20 | $4.25 \pm 2.04$ | 28.7 | 19 | $3.57 \pm 2.24$ | 36.8 | 39 | $3.92 \pm 2.14$ | 32.4 |
| 6&7 | Fluoride free water | Natural | 25 | $5.96 \pm 1.39$ | — | 26 | $5.65 \pm 2.36$ | — | 51 | $5.80 \pm 1.93$ | — |
| 8 | 200 ppm $Al^{+3}$ + 0.1% malic acid | 7.9 | 16 | $3.37 \pm 2.06$ | 43.5 | 17 | $3.94 \pm 1.81$ | 30.3 | 33 | $3.67 \pm 1.93$ | 36.7 |

We claim:

1. A method for reducing the incidence and severity of dental caries comprising the application to the teeth of a preparation comprising:

an anticariogenically effective and non-toxic amount of at least one water-soluble aluminum salt;

a non-toxic amount of a member selected from the group consisting of stable carboxylic acids and water-soluble salts thereof; and a carrier suitable for use in the oral cavity, the pH of said composition lying in the range of about 7.0–9.0, and the molar ratio of complexing carboxylic acid or salt thereof to aluminum ion being at least about 1.1.

2. A method, as claimed in claim 1, wherein the member is malic acid.

3. A method, as claimed in claim 1, wherein the member is tartaric acid.

4. A method, as claimed in claim 1, wherein the carrier comprises a cleaning and polishing agent.

5. A method, as claimed in claim 1, wherein the aluminum is present at a level of about 0.001–5.0%, by weight, calculated as aluminum ions, and the member is present at a level of about 0.05–25%, by weight.

6. A fluoride-free anticariogenic oral composition comprising:

an anticariogenically effective and non-toxic amount of at least one water-soluble aluminum salt;

a non-toxic amount of a member selected from the group consisting of stable complexing carboxylic acids and water-soluble salts thereof; and a carrier suitable for use in the oral cavity, the pH of said composition lying in the range of about 7.0–9.0, and the molar ratio of complexing carboxylic acid or salt thereof to aluminum ion being at least about 1:1.

7. An oral composition, as claimed in claim 6, wherein the member is malic acid.

8. An oral composition, as claimed in claim 6, wherein the member is tartaric acid.

9. An oral composition, as claimed in claim 6, wherein the carrier comprises a cleaning and polishing agent.

10. An oral composition, as claimed in claim 6, wherein the aluminum is present at a level of about 0.001–5.0%, by weight, calculated as aluminum ions, and the member is present at a level of about 0.05–25%, by weight.

* * * * *